(12) United States Patent
Kirk

(10) Patent No.: US 7,338,474 B2
(45) Date of Patent: Mar. 4, 2008

(54) LUER ATTACHMENT FOR SYRINGE SAFETY

(75) Inventor: Kevin F. Kirk, Walled Lake, MI (US)

(73) Assignee: Tribute Technologies, LLC, Franklin, MI (US)

( * ) Notice: Subject to any disclaimer, the term of this patent is extended or adjusted under 35 U.S.C. 154(b) by 438 days.

(21) Appl. No.: 10/769,955

(22) Filed: Feb. 2, 2004

(65) Prior Publication Data
US 2004/0162530 A1 Aug. 19, 2004

Related U.S. Application Data

(60) Provisional application No. 60/447,990, filed on Feb. 18, 2003.

(51) Int. Cl.
A61M 5/00 (2006.01)
A61M 5/31 (2006.01)

(52) U.S. Cl. ................ 604/240; 604/48; 604/93.01; 604/181; 604/187

(58) Field of Classification Search ............... 604/192, 604/198, 240, 110, 187
See application file for complete search history.

(56) References Cited

U.S. PATENT DOCUMENTS

| | | | |
|---|---|---|---|
| 5,460,611 A | | 10/1995 | Alexander |
| 5,720,727 A | * | 2/1998 | Alexander et al. .......... 604/110 |
| 6,817,989 B2 | * | 11/2004 | Svendsen et al. .......... 604/192 |
| 2003/0121812 A1 | * | 7/2003 | Sprieck et al. .............. 206/365 |

* cited by examiner

Primary Examiner—Phillip Gray (57) ABSTRACT

The needle head assembly is used with an ISO luer lock or luer slip syringe having a single thread or multiple threads. The assembly includes a one or two piece luer needle housing having a plunger end, a needle end and a pair of opposing slots located at the needle end thereof. A plunger is axially movable relative to the upper end of the luer needle housing. A needle holder assembly is located in the needle end of the needle housing, with the holder assembly including a bridge fixed in the needle end of the needle housing. The bridge includes a needle holder that has portions extending in opposite directions from the bridge. A diaphragm with a center aperture is sleeved over one of the portions of said needle holder which faces the plunger end of the needle housing. The needle holder has a center passage which permits a needle to be inserted and secured in position at the time of assembly. The one portion of the needle holder extends toward the plunger end of the needle housing thereby permitting different gauges of needles to be used with only one size of diaphragm.

52 Claims, 5 Drawing Sheets

LUER ATTACHMENT FOR SYRINGE SAFETY

CROSS REFERENCE TO RELATED APPLICATIONS

This application claims the benefit of U.S. Provisional Patent Application No. 60/447,990 filed Feb. 18, 2003.

BACKGROUND OF THE INVENTION

1. Field of the Invention

The present invention relates to syringes and particularly to safety syringes designed for shielding the needles of the syringes to prevent accidental sticks and to further comply with "The Needle Stick Safety & Prevention Act" enacted into Federal law in the year 2000.

2. Prior Art

It is well known that the risk of contracting diseases such as hepatitis and HIV from accidental sticks with dirty needles is a potentially deadly hazard for medical personnel. The prior art has many syringe designs that attempt to avoid accidental sticks. Such syringes generally have three goals. One goal is to minimize the window of opportunity for an accidental stick. Another goal is that the syringe should be simple to operate and preferably operate as similarly as possible to a conventional syringe. The final goal is that the safety syringe should be easy to manufacture and assemble.

One prior art device is the Alexander U.S. Pat. No. 5,460,611 entitled "Safety Syringe" which issued on Oct. 24, 1995. Another prior art device is the Alexander et al U.S. Pat. No. 5,720,727 entitled "Safety Syringe" which issued on Feb. 24, 1998. Such prior art devices include a syringe which will automatically cover the needle upon the administering of the injection to the patient. Each of the Alexander patents identify many prior art patents and disclose devices directed in part to preventing dirty needle sticks.

SUMMARY OF THE INVENTION

It is a feature of the invention to provide a disposable needle head assembly which fits onto ISO (International Standard Organization) luer lock and luer slip syringes, with the needle head assembly having six separate parts including a luer needle housing, a needle, a plunger, an actuator sheath combination, a diaphragm and a cover cap. These parts when assembled form an attachable luer safety needle head assembly that covers the sharp end of the needle with a sheath while it remains in the patient's tissue, thus providing protection against accidental needle stick puncture wounds after the needle is removed from a patient's body.

Another feature of the invention is to provide a disposable needle head assembly having a luer needle housing in the form of a cylindrical tubular body having an outer walled surface, with the upper end protruding outwardly from the center point or axis and providing a single ISO thread or a plurality of ISO luer threads which are of the same configuration as the threads utilized in preexisting luer needle cups. The purpose of the ISO thread or threads is to allow the needle head assembly to attach to the barrel of a luer lock syringe by means of a clockwise twist or rotation.

Still another feature of the invention is to provide a bridge at the needle end of the generally cylindrical tubular body forming the luer needle housing. The bridge has a needle holder that protrudes both upwards and downwards in opposite directions from the bridge. The needle holder has a center passage, which allows a needle to be inserted and secured therein or glued into position at the time of assembly. A portion of the needle holder that protrudes upwardly towards the plunger of the needle head assembly provides the means for allowing many different gauges of needles to be used with only one size diaphragm. In other devices, the needle holder only faces downward, towards the needle end of the syringe. Such a construction prevented the attachment of multiple gauges and lengths of needles to the same total assembly since individual diaphragms of various sizes had to be used to accomplish the end result. Thus, each separate gauge size of needle required a separate aperture size in the diaphragm.

Still another feature of the invention is that the downward protrusion of the needle holder has a tapered or flared entrance into the center passage. This feature permits the needle to be inserted with greater ease. The invention uses only one size diaphragm which is made of soft rubber and has an aperture down its center or middle. The diaphragm aperture remains constant in diameter size and fits perfectly over the upper portion of the needle holder creating an air-tight fit.

A further feature of the present invention is to provide a disposable needle head assembly wherein the diaphragm which is located in the luer needle housing is provided with a hollow cavity located between the outer diameter wall and the inner wall that houses the hole for the needle holder. At the bottom of the outer wall of the diaphragm is a lip that protrudes inward. The assembly further includes an actuator which has at one end a hollow sheath that is formed by extrusion from the actuator hub and fits over the needle. The sheath-actuator or actuator sheath is able to slide freely without constraint over the needle.

A still further feature of the invention is to provide an actuator which has at one end a hollow sheath, which is formed by an extrusion from the actuator hub and fits over the needle. The sheath and actuator slide freely without constraint over the needle, with the sheath being slightly larger in diameter than the needle diameter and tapered at its point end. This taper is provided so as not to create any extra pain during an injection. At the opposite end of the actuator hub are a pair of protruding legs. When assembled, the legs straddle the bridge and the needle holder, with outer portions of the actuator legs extending through opposing slots located in the luer needle housing.

According to the present invention, there is provided a needle protection assembly of the above-specified kind, specifically a needle head assembly or a combination of a safety syringe and a needle head assembly, characterized in that the needle head assembly is for use with an ISO luer lock or luer slip syringe. The needle head assembly comprises a luer needle housing consisting of one or two parts. The housing has a plunger end and a needle end. A plunger is axially moveable relative to the plunger end of the luer needle housing. A needle holder assembly is located in the needle end of the housing, with the assembly including a bridge fixed in the needle end of the luer needle housing. The bridge includes a needle holder that has portions extending in opposite directions from the bridge. A diaphragm with a center aperture is sleeved over one of the portions of the needle holder which faces the plunger end of the needle housing. The needle holder has a center passage which permits a needle to be inserted and secured such as by gluing into position at the time of assembly. One portion of the needle holder extends towards the plunger end of the needle housing thereby permitting different gauges of needles to be used with only one size of diaphragm. An actuator is provided which has an annular hub with a hollow sheath at one end and a pair of protruding legs at the other end. The diaphragm has a hollow cavity located between the outer diameter wall of the diaphragm and the inner wall of the diaphragm for receiving the protruding legs of the actuator. The actuator is located in the needle end of the housing where the legs surround the bridge and needle holder. Outer portions of the actuator legs may be provided with slots or serrations forming finger and thumb rests. The leg portions extend through opposing slots provided in the lower end of the luer needle housing.

Another feature of the present invention is to provide a disposable needle head assembly which is usable on ISO luer lock and luer slip syringes and which is protectively contained during injection into a patient as well as during and after injection into a vial of medication.

A final feature of the present invention is to provide a disposable needle head assembly which is simple in construction, economical to manufacture and is efficient in operation.

DETAILED DESCRIPTION OF THE PREFERRED EMBODIMENT OF THE INVENTION

Figures 1, 2, 3, 4:
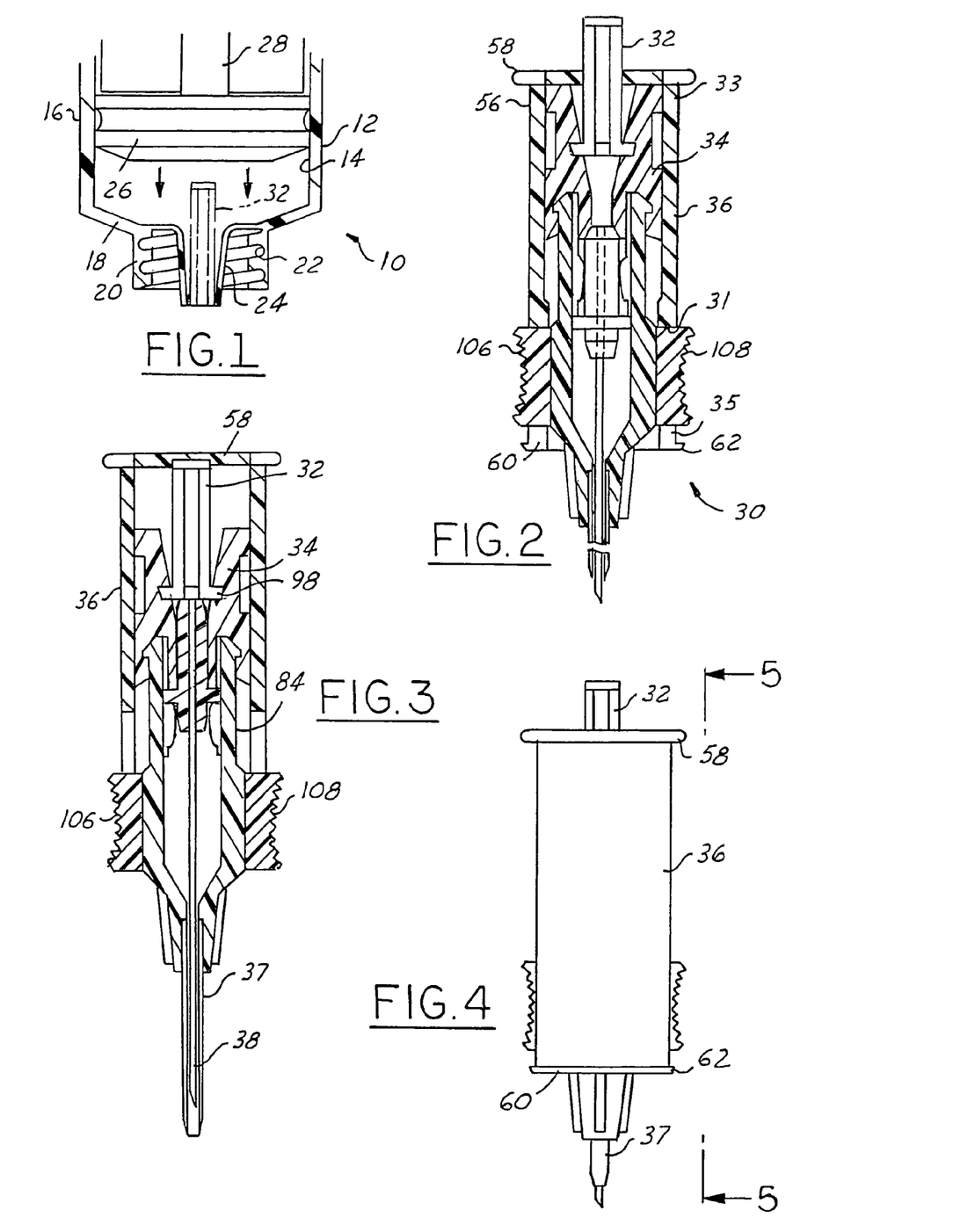
FIG. 1 is a fragmentary view of a conventional safety syringe showing the lower portion thereof including the barrel, plunger or rod and piston and the nozzle or cone of a luer lock cup provided at the bottom of the barrel. The plunger from the disposable needle head assembly is shown in dotted lines extending through the nozzle or cone of the luer lock cup into the barrel.
FIG. 2 is a vertical sectional view through the disposable needle head assembly in an inactivated or inoperative position.
FIG. 3 is a vertical sectional view through the disposable needle head assembly in an activated or operative position.
FIG. 4 is an elevational view of the needle head assembly in an inactivated position and illustrating the pair of serrated finger slots provided on the actuator extending through slots, not shown, provided in the luer needle housing.

Referring to FIG. 1, there is illustrated a fragmentary sectional view of a conventional safety syringe 10. Only the lower portion of the safety syringe 10 is illustrated. It comprises a substantially hollow barrel 12 having an interior wall 14 and an exterior wall 16. The bottom wall 18 of the barrel 12 is tapered and terminates in a luer lock cup 20 having a plurality of threads 22. The bottom wall of the barrel 12 has a centrally located funnel or cone 24 which extends through the luer lock cup 20 and has a length greater than the height of the cup 20 as illustrated in FIG. 1. Moveably mounted within the barrel 12 is a piston or plunger 26 and a piston rod 28. The bottom wall 18, piston 26 and the interior wall 14 define a fluid or liquid receiving cavity within the barrel 12. In a preferred embodiment calibrated measurement lines, not shown, are marked on the exterior wall 16. The barrel 12 is preferably made from a translucent plastic material. The piston rod 28 extends through an opening provided in the top end of the barrel 12. The rod 28 has a thumb end, not shown. The piston 26 is sized to engage the interior wall 14. The piston 26 is made or covered with rubber while the piston rod 28 is made of plastic material. It is well known that upon insertion of the piston 26 and rod 28 into the barrel 12, the volume of the fluid receiving cavity may be varied by actuating the plunger or rod 28.

The needle head assembly 30 is illustrated in an inoperative or non-actuated position in FIGS. 2, 4, 5, 16 and 18. The inoperative position is readily illustrated by the fact that the upper end of the needle plunger 32 extends above the top of the luer needle housing 36. When the needle head assembly 30 is connected to the safety syringe 10, the needle plunger 32 extends through the cone 24 of the safety syringe 10 into the cavity of the barrel 12 as is represented by the dotted lines in FIG. 1. The plunger or stem 32 will feed into the nozzle or cone 24 and as such provides the means of activation when depressed by the piston 26.

Figure 12:
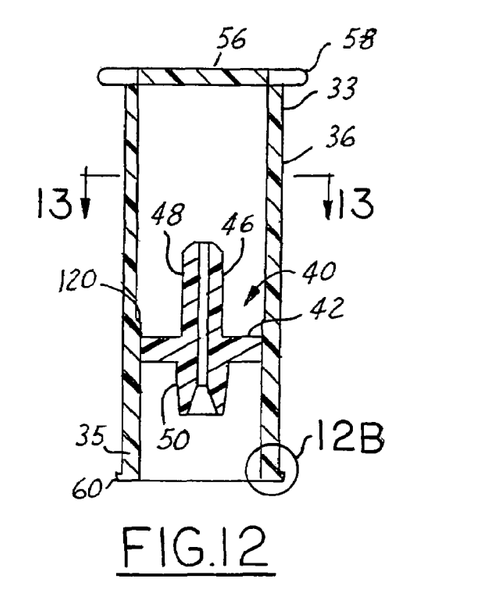
FIG. 12 is a cross sectional view of the luer needle housing or cylinder and illustrating the bridge and needle holder assembly mounted in the interior thereof.
Figure 14:
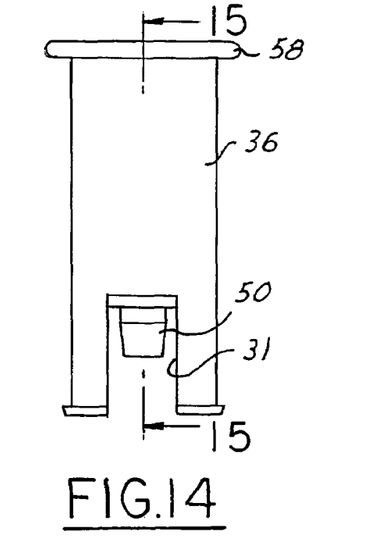
FIG. 14 is an elevational view of the luer needle housing and illustrating an ISO thread at the plunger end thereof and opposing slots in the needle end thereof.
Figure 15:
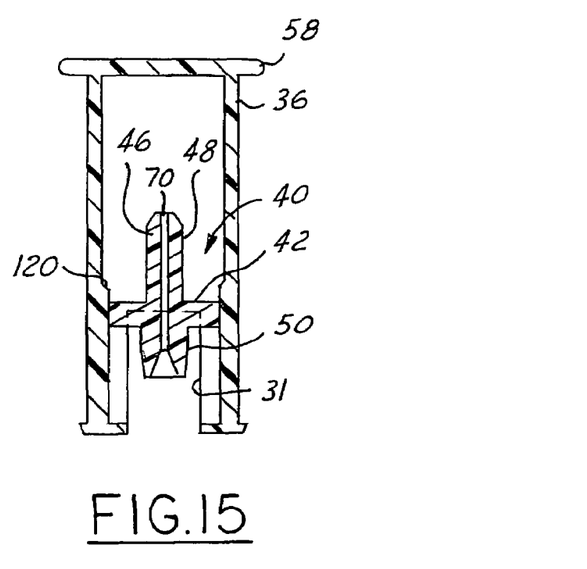
FIG. 15 is a cross sectional view taken on the line 15-15 of FIG. 14.

The needle head assembly 30 is composed or assembled from six separate parts, including the needle plunger 32, diaphragm 34, luer needle housing 36, an actuator sheath 37, a needle 38 and a cover cap 39. The luer needle housing 36 has a plunger end 33 and a needle end 35 as shown in FIG. 2. The needle plunger 32 is axially movable relative to the plunger end 33 of the luer needle housing 36. A needle holder assembly 40 (FIG. 12A) is located in the needle end 35 of the needle housing 36 as shown in FIG. 12. Housing 36 has a pair of slots or openings 31 (FIGS. 14 and 15) for inserting the holder assembly 40 into the needle housing 36. The holder assembly 40 includes a bridge 42 which is fixed in the needle end 35 of the luer needle housing 36. The bridge 42 includes a needle holder 46 that has portions 48 and 50. The portion 48 is of a length greater than the portion 50. The portions 48 and 50 extend in opposite directions from the bridge 42. The resilient diaphragm 34 (FIG. 8) with a center passage or aperture 52 is sleeved over the needle holder portion 48 which faces the plunger end 33 of the luer needle housing 36.

The luer needle housing 36 has located on the outer walled surface 56 and protruding outward from the center point or center line a single ISO luer thread 58 as shown in FIG. 2. This thread 58 is to allow the luer needle housing 36 to attach or connect to the luer lock 20 of the luer lock barrel 12 by means of a clockwise twist. This provides a tight seal between any ISO luer lock syringe barrel and the luer needle housing 36. The connection could be provided by hand or machine depending on its intended purpose or packaging. The barrel of the luer needle housing 36 will stay constant in diameter as well as the ISO luer thread 58 located at its top. This will insure that the corresponding coupling threads 22 located on the luer syringe barrel 12 fit perfectly. A luer connection is well known in the field of medicine and medical manufacturing.

The luer needle housing 36 further include at the needle end 35 a bottom or outer wall 60 through which the needle 38 extends. The outer wall 60 is provided with a small ridge 62 that runs the entire circumference of the luer needle housing 36. The ridge 62 is provided to keep the needle cover 39 (FIG. 5) in a semi-locked position. The needle cover 39 has a corresponding ridge 64 on its inner surface that runs its entire circumference. Together the needle cover ridge 62 and the luer needle-housing ridge 64 create a semi-locking barrier. By pulling lightly on the needle cover 39 this barrier can be over ridden and the cover cap 39 removed so to expose the sharp needle 38 for processing an injection. It is suggested that the luer needle housing 36 be attached to the syringe barrel 12 before this act is commenced. Semi-locking the needle cover 39 in place on the luer needle housing 36 ensures that a pre-injection needle stick injury does not occur in general handling. The needle cover 39 also has longitudinal ridges 66 located around the uppermost outer circumference. The ridges 66 have been placed to keep the needle cover 39 from rolling when placed on a flat surface. The length of the needle 38, which is pre-mounted in the luer needle housing 36 during assembly, will determine the length of the needle cover 39. The needle cap 39 (if so deemed by its manufacture) may be outfitted with its own top cap 68 (FIGS. 17 and 18) to prevent it from contamination when used in a field operation.

The needle holder 40 (FIGS. 12 and 12A) has a center passage 70 which permits the needle 38 to be inserted and glued into position at the time of assembly. One portion 48 of the needle holder 40 extends towards the plunger end 33 of the needle housing 36 thereby permitting different gauges of needles to be used with only size of the diaphragm 34.

In other devices on the market, the needle holder only faces downward, towards the needle end of the syringe barrel. This prevented the attachment of multiple gauges and lengths of needles to the same total assembly. This is because different individual diaphragms had to be used to accomplish this objective. Each separate gauge size required a separate aperture size in the diaphragm.

Figure 12A:
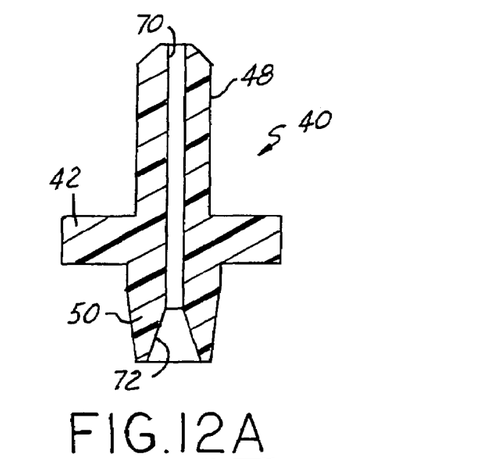
FIG. 12A is an enlarged view, in cross section, of the needle holder and bridge assembly shown installed in the housing of FIG. 12.
Figure 12B:
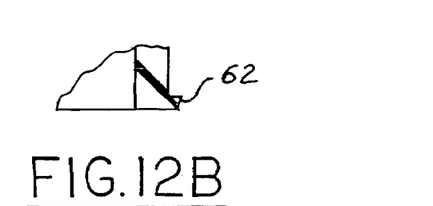
FIG. 12B is an enlarged view, in cross section, of the lower portion of the luer needle housing.
Figure 13:
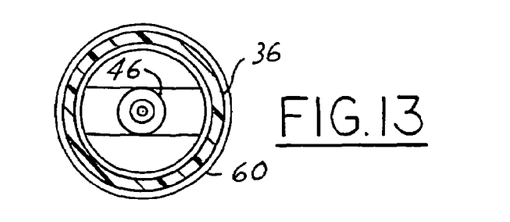
FIG. 13 is a cross sectional view taken on the line 13-13 of FIG. 12.

The downward protrusion 50 of the needle holder 40 has a flared or tapered entrance 72 in the center passage 70. This is provided so a needle can be inserted with greater ease. The invention uses only one size diaphragm 34, which is made of soft rubber and has an aperture 52 down its middle or center. The aperture 52 varies in diameter where needed and fits perfectly over the upper portion 48 of the needle holder 46. It allows fluid to pass from the syringe barrel 12 into and through the needle 38 when pressure is applied to the needle plunger 32 upon actuation of the piston 26 and rod 28 of the syringe 10. By using this method of a needle holder and a constant sized center aperture diaphragm, one sized diaphragm can fit all needle sizes. In other words, it is apparent that individual sized needles and diaphragms would not have to be used for each application.

Figures 5, 6, 7, 8, 9, 10, 11:
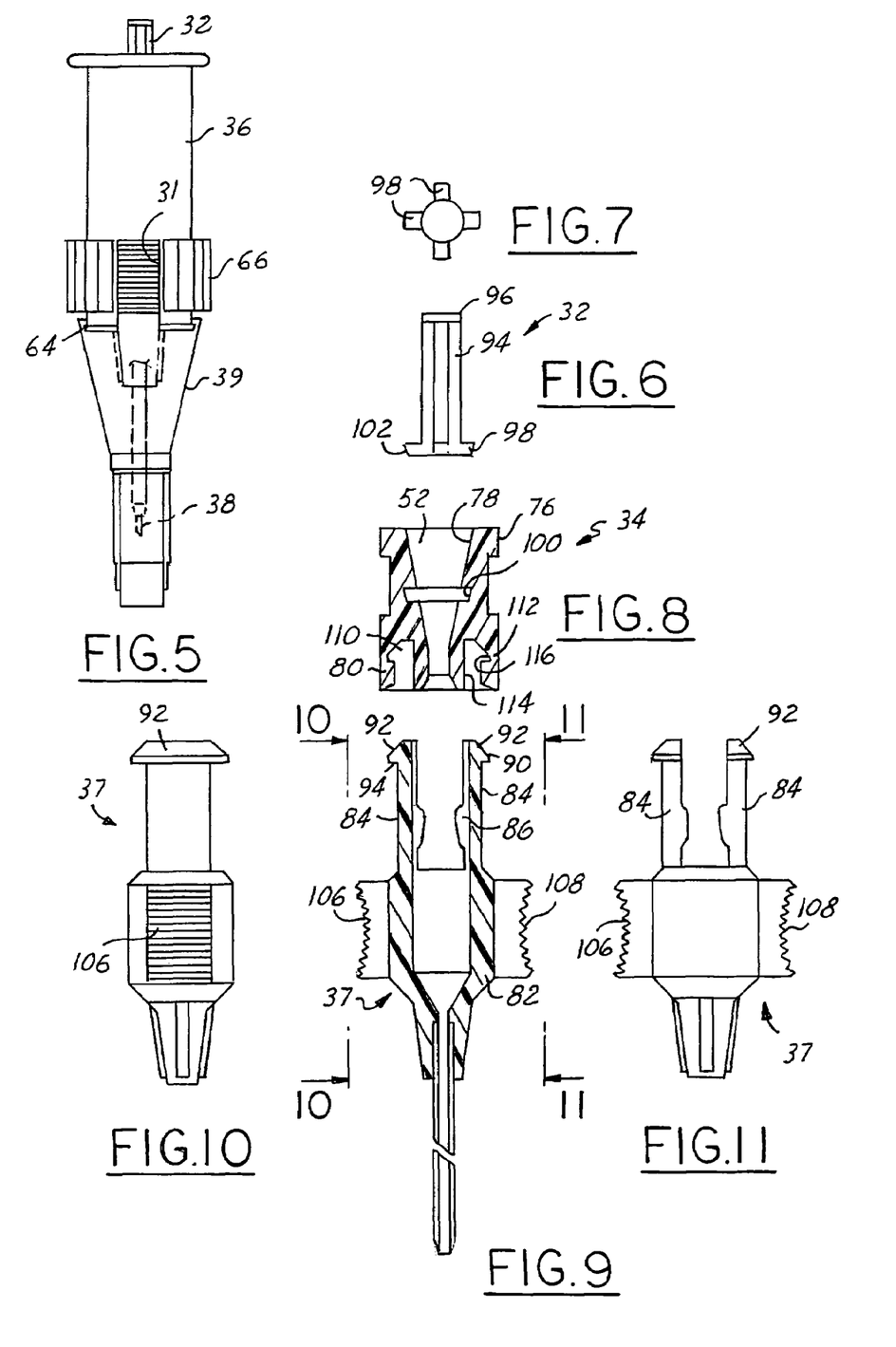
FIG. 5 is an elevational view of the needle head assembly in an inactivated position looking in the direction of arrows 5-5 of FIG. 4 and illustrating one of the finger slots and the cover cap enclosing the needle.
FIG. 6 is an elevational side view of the needle plunger.
FIG. 7 is a top view of the needle plunger of FIG. 6 and illustrating the four feet or feet-like extensions.
FIG. 8 is a vertical sectional view through the diaphragm which is designed to accept both the needle plunger of FIG. 6 and the actuator sheath unit of FIG. 9. It has a 6% luer cone at the top thereof to allow the cone of a luer syringe when screwed onto the actual housing itself to fit down into the diaphragm.
FIG. 9 is a vertical sectional view through the unitary actuator and sheath assembly.
FIG. 10 is an elevational view of the actuator and sheath assembly looking in the direction of arrows 10-10 of FIG. 9.
FIG. 11 is a front elevational view of the actuator and sheath assembly looking in the direction of arrows 11-11 of FIG. 9.

As shown in FIG. 8, the diaphragm 34 has a hollow cavity or aperture 52 located between the outer diameter wall 76 and the inner diameter wall 78 that houses the hole for the needle holder 40. At the bottom of the outer wall 76 of the diaphragm 34 is a lip 80 that protrudes inward, towards its inner wall 78. This lip 80 locks the actuator sheath 37 in place, once it is placed over the bridge 42 and the legs 84 of the actuator 37 are pushed into the diaphragm 34. Using this method of connection, diaphragm 34 to actuator sheath (which protrudes by means of extension from the actuator) is lockable, prohibiting movement in both ingress and egress directions. In other devices, one could physically or accidentally move, bump or push the sheath into the covered position before an injection could be formed.

The actuator sheath 37 has at one end a hollow sheath, which is formed by extrusion from the actuator hub 82. The sheath fits over the needle 38. The actuator sheath 37 slide freely without constraint over the needle 38. The sheath is slightly larger in diameter than the diameter of the needle 38 and is tapered at its point end. The taper is provided so as not to create any extra pain in a patient during an injection. At the opposite end of the actuator hub 82 are located two protruding legs 84. When assembled, the legs 84 straddle the bridge 42 and the needle holder assembly 40, located in the luer needle housing 36.

The legs 84 have two sets of locking protrusions. The first set of protrusions 86 is located approximately half way up the legs 84 as best illustrated in FIG. 9. The first set of protrusions 86 is formed on the legs for two purposes. The first purpose is to keep the actuator sheath 37 from activating prematurely. Such premature activation may happen from minor pressure placed on the plunger 32 or diaphragm 34 during normal operations. The second purpose for the first set of projections 86 is to lock the actuator legs 84, hub 82 and needle sheath in the down or covered position after an injection has been performed on a patient as shown in FIG. 3.

The actuator 37 further includes a second set of protrusions 90 which is located at the ends of the actuator legs 84 and faces in an outward direction from the center point or center line of the actuator. The second set of protrusions 90 are tapered at their top edges 92 to allow the protrusions 90 easy access into the cavity 110 of the diaphragm 34. The bottom edges 94 of the second set of protrusions 90 are formed at a 90° angle from the actuator legs 84. This angle or lip causes the actuator legs 84 to lock with the lip provided on the inner side of the outer diameter wall of the diaphragm 34 when the actuator 37 and diaphragm 34 are assembled. Once this procedure has been performed, the actuator 37 and diaphragm 34 act and move as one mechanism or unit.

The needle plunger 32 and the luer needle housing 36 of the needle head assembly 30, when assembled, locks the needle plunger in the down position after an injection of fluid into a patient thereby rendered the device unusable.

The needle plunger 32 has four walls 94, each facing 900 from one another much like most syringe plungers. The four walls 94 create a pedestal for the plunger's top and bottom. At the top is located a cap 96 used for the purpose of applying downward pressure on the plunger 32 when the piston 26 and rod 28 are activated. The needle plunger 32 could also be made from a solid cylindrical post.

At the bottom of the pedestal walls 94 of the plunger 32 are four feet-like extensions 98 for the purpose of seating itself into an upper channel 100 provided in the diaphragm 34. The feet-like extensions 98 are beveled or angled at 102 thereby permitting easy access of the feet extensions 98 in the diaphragm's upper channel 100. Once the feet-like extensions 98 are seated into or onto the diaphragm's upper channel 100, when actuated, fluid passes through the diaphragm's center aperture and in between each of the four walls 94 of the needle plunger 32 to minimize the loss of flow into the needle cavity. The feet-like extensions 98 act as a base and locking system for the diaphragm 34 whereby the plunger 32 and diaphragm 34 move together as one mechanism when pressure is applied to the plunger 32 by the rod 28 and piston 26 of the safety syringe 10. When the safety syringe 10 is actuated, the piston 26 of the syringe 10 makes contact with the plunger 32 of the needle head assembly 30 thereby activating the actuator sheath 37 and needle 38 by means of the downward pressure applied.

The actuator hub 82 is provided with a pair of opposing finger slots 106, 108 which move with the actuator sheath 37 since the finger slots 106, 108 are an integral part thereof. The finger slots 106, 108 are optional. The purpose of the finger slots 106, 108 is to provide a means whereby the user can place a finger and thumb on opposite sides and physically push the actuator sheath 37 forward over the top of the bare needle 38. Once the needle plunger 32 has been pushed down, it pushes the diaphragm 34 and actuator sheath 37 all in one motion covering the end of the needle 38. At the same time, the two finger slots 106-108 are also pushed down because they are a part of the actuator sheath 37. If the manufacturer desires not to have the finger slots, the device would still be actuated by means of the syringe's rod 28 and piston 26. Thus, the finger slots 106, 108, which are serrated, provide an extra means of activation. The finger slots do not need to be serrated but it is believed that the serrations will provide a better grip on the two finger slots.

The diaphragm 34 also has a hollow cavity 110 located between the outer diameter wall 112 and the inner diameter wall 114 that houses the hole for the needle holder 40. At the bottom of the outer wall 112 of the diaphragm 34 is a lip 116 that protrudes outward towards its outer wall 112. This lip 116 locks the actuator sheath 37 in place, once it has passed over the bridge 42 and the length of the actuator 37 is pushed into the diaphragm 34. By using this method of connection, diaphragm 34 to actuator sheath 37, the sheath (which protrudes by means of extrusion from the actuator) is lockable. This locking prohibits movement in both ingress and egress directions. In other devices, this means of locking is not performed since one can physically or accidentally, move, push or bump the sheath up into the covered position before an injection can be performed.

At the opposite or top end of the diaphragm 34 is a 6% ISO luer tapered aperture 78. This 6% nozzle like aperture 78 conforms to the luer nozzle 24 that protrudes from a standard ISO luer syringe 10. This opening creates a seat on which an airtight fit between the needle head assembly 30 and the luer syringe 10 can take place. Just pass the bottom of a 6% aperture 78 in the channel or opening 100 running the entire circumference of the diaphragm. This channel 100 is provided for the acceptance of the needle plunger 32 and the four feet 98 located at the bottom of the plunger 32. By placing pressure on the needle plunger 32, seating of the four feet 98 into the diaphragm channel 100 can be accomplished. Once the assembly procedure of all three parts has been performed (the needle plunger, actuator sheath and diaphragm), they act and move as one mechanism or unit. The assembly of these parts in the luer needle housing 36 is separate from the syringe. This assembly allows a technician using this device to choose an assortment of needle gauges and lengths, while still maintaining the syringe cc size that was chosen for the application. This is believed to be the first ISO luer needle that accomplishes both interchangeable and safety features in one small unit.

The needle housing 36 further includes an internal ridge 120 which along with the bridge 42 (FIG. 12), prevents the actuator sheath 37 from exiting the needle housing 36. The actuator sheath 37 is inserted through the bottom of the needle housing 36, while the diaphragm 34 and plunger 32 are inserted through the top of the needle housing 36.

Second Embodiment

On the outer wall of the luer needle housing 36 located near the needle end 35 is a small ridge 62 that runs the entire circumference of the luer needle housing 36. This ridge 62 has been placed to keep the needle cover 39 in a semi-locked position. The needle cover 39 has a corresponding ridge 64 (FIG. 5) on its inner surface that runs its entire circumference. Together the needle cover ridge 64 and the luer needle housing ridge 62 create a semi-locking barrier. By pulling lightly on the needle cover 39, this barrier can be over ridden to expose the needle 38 from processing an injection. It is recommended that the luer needle housing 36 be attached to the syringe barrel 12 before this act is commenced. Semi-locking the needle cover 39 in place on the luer needle housing 36 insures that a pre-injection needle stick injury does not occur in general handling. The needle cover 39 also has longitudinal ridges 66 located around the uppermost outer circumference. The ridges 66 have been placed to keep the needle cover 39 from rolling when placed on a flat surface. The length of the needle 38, which is premounted in the luer needle housing 36 during assembly, will determine the length of the needle cover 39. The cover 39 (if so deemed by its manufacturer) may be outfitted with its own top cap 68 to aid it from contamination when used in a field operation.

The sheath-actuator 37 itself has at one end a hollow sheath that is formed by extrusion from the actuator hub 82 and fits over the needle 38. The sheath may be a separate part that is welded to the actuator rather than extruded. The sheath-actuator 37 slides freely without constraint over the needle 38. The sheath is just slightly larger in diameter than the needle diameter and is tapered at its point end. This is provided so as not to create any extra pain during an injection.

Another embodiment of the present invention is illustrated in FIGS. 18-24 inclusive where the same numerals used in the preceding embodiment will be utilized to designate corresponding parts. If a part or component has been modified, the same number will be used with a prime designation -'- to designate a modified but similar part. This embodiment uses a modified needle plunger 32', a modified diaphragm 34' and a modified luer needle housing 36'. The remaining three components, namely, the actuator sheath 37, needle 38 and cover or needle cap 39 were not modified and remain the same.

Figures 16, 17, 18, 19:
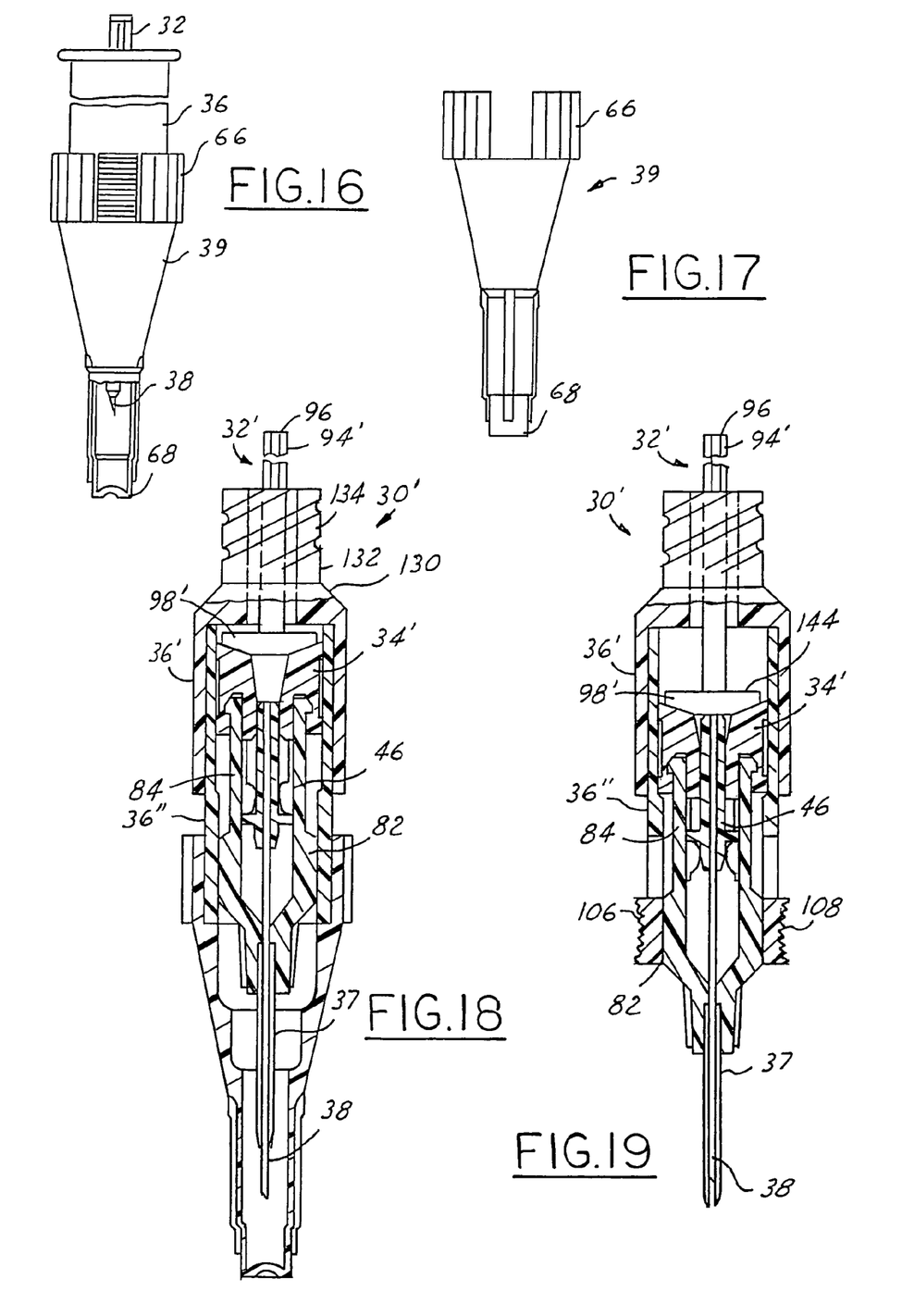
FIG. 16 is an elevational view of the disposable needle head assembly in an inoperative position and with a cover cap positioned over the needle end of the assembly.
FIG. 17 is an elevational view of the cover cap.
FIG. 18 is another embodiment of the present invention showing a vertical sectional view of the disposable needle head assembly in an inoperative position.
FIG. 19 is a vertical sectional view similar to FIG. 18 but showing the needle head assembly in an activated position.
Figures 20, 21:
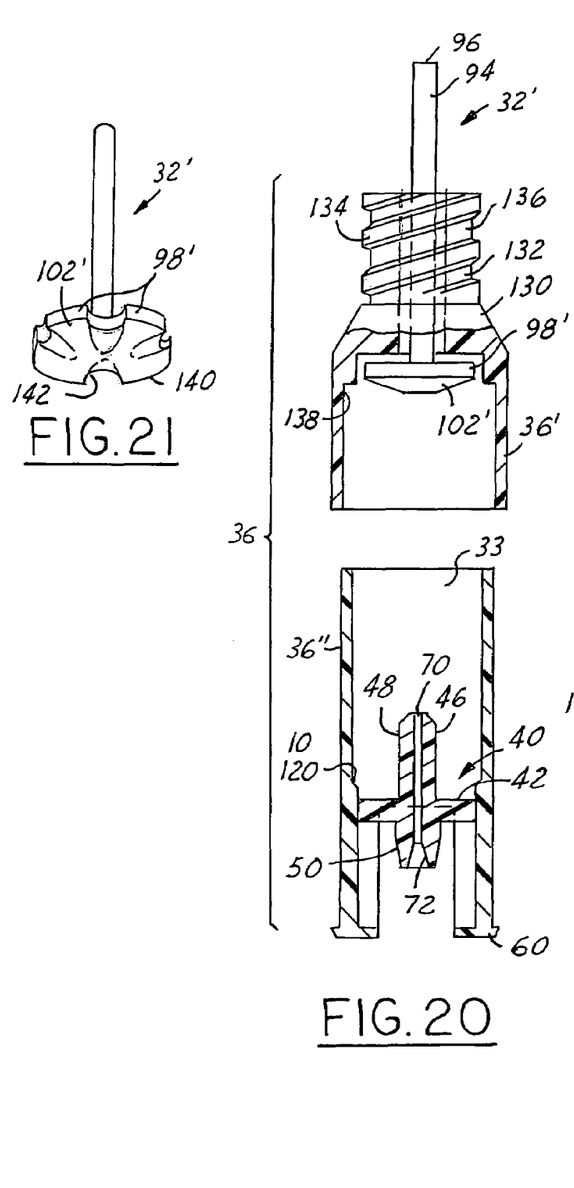
FIG. 20 is a vertical sectional view of the unassembled upper and lower parts of the needle housing showing on the upper housing part a plurality of locking threads and a plunger having on the inner end thereof a slotted circular base permitting fluid from the syringe to pass into the diaphragm and needle assembly of the lower housing part.
FIG. 21 is a perspective view of the plunger and slotted circular base.

The modified luer needle housing is divided into an upper housing part 36' and a lower housing part 36". The lower housing part 36" is of generally cylindrical configuration and fits within the inside diameter of the upper housing part 36' as shown in FIGS. 18-20 inclusive. The upper housing part 36' on the exterior thereof has a truncated surface 130 and a tubular stem 132 provided with a plural threaded luer connection 134 comprising a plurality of threads 136 rather than a single thread 58 as provided in the preceding embodiment. The threads 136 allow the upper housing part 36' to be attached or connected to the luer lock on a luer lock barrel 20. This provides a tight seal between the ISO luer lock syringe barrel 20 and the luer needle upper housing part 36'.

The upper housing part 36' has an internal cavity 138 in which the lower housing part 36" is received. The external luer lock connection 134 and tubular stem 132 have a passageway which receives the telescoping needle plunger 32'. When the needle head assembly 30' (FIGS. 18 and 19) is connected to a safety syringe, the needle plunger 32' extends through the cone of the safety syringe into the cavity of the barrel as explained previously in connection with the first embodiment. The plunger 32' will feed into the nozzle or cone 24 (FIG. 1) and as such provides the means of activation when depressed by the piston 26 provided in the syringe 10.

Figure 22:
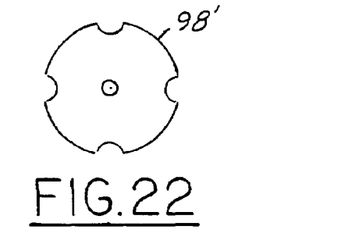
FIG. 22 is a top view of the plunger and circular base of FIG. 21.
Figure 23:
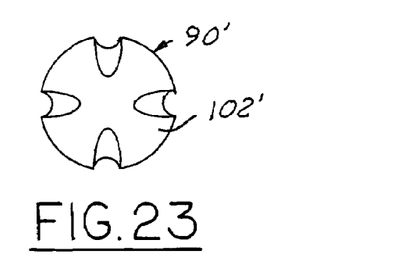
FIG. 23 is a bottom view of the plunger and circular base of FIG. 21.

The needle plunger 32' has four walls 94, each facing 90° from one another much like most syringe plungers. The walls 94 create a pedestal for the plunger's top and bottom. A cap 96 is formed at the top for applying downward pressure to the plunger 32' when the piston and rod are activated. The plunger 32' may have a different configuration such as being made from a solid cylindrical post or rod.

Figure 24:
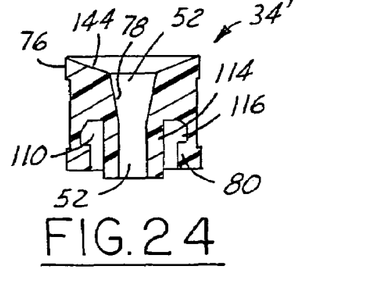
FIG. 24 is a vertical sectional view through the diaphragm employed in FIGS. 18 and 19.

The plunger 32' is provided at the bottom thereof with a circular base 140 having provided therein a plurality of legs 98' (four in number), with each leg 98' having a part conical surface 102'. Thus, the circular base 140 has the legs 98' spaced apart to provide slots or passages 142 which receive fluid from the syringe to pass into the diaphragm 34' and needle assembly of the lower housing part 36". The conical surfaces 102' of the circular base 140 are adapted to seat on the upper conical surface 144 surrounding the entrance to the diaphragm's center passage or aperture 52, as best illustrated in FIGS. 20 and 24. With such a construction the plunger 32' and the conical surfaces 102' seat on the top surface 144 of the diaphragm 34' of FIG. 24. Once the plunger base 140 is seated onto the diaphragm's upper surface 144 surrounding the aperture 52, when activated, fluid passes through the diaphragm's center aperture 52 and between each of the four walls 94 of the needle plunger 32' to minimize the loss of flow into the needle cavity. The seated plunger 32', diaphragm 34' and actuator sheath 37 move together as one mechanism when pressure is applied to the plunger 32' by the rod and piston of the safety syringe.

When the safety syringe is actuated, the piston of the syringe make contact with the plunger 32' of the needle head assembly 30' thereby activating the actuator sheath 37 and needle 38 by means of the downward pressure applied.

SEQUENCES TO ACTIVATE

The sequences of events to activate the needle head assembly 30 or 30' are as follows:

1. Choose the length and gauge of the needle desired for the procedure.
2. Open packaging.
3. While cover-cap is still attached, place the needle plunger that protrudes from the top of the body into the same opening of the syringe luer nozzle.
4. Turn the assembly clockwise to seat it properly on the luer syringe.
5. Remove the needle cover cap.
6. Fill syringe normally and exhaust any air within the syringe and needle, consistent with normal procedure.
7. Inject the patient normally making sure the syringe plunger has been depressed to its fullest point.
8. Remove guarded needle from patient without fear of puncture injury and discard entire unit in the closest sharps container.

The scope of this invention not only protects the end user by means of covering the sharps end of the needle after use but also protects maintenance and sanitary workers who may come in contact with this type of refuse. By providing additional locking features, this invention also meets all of the OSHA standards. The standards set forth by OSHA explain what the ultimate safety syringe would do. One-handed use is recommended. Handled or prepared the same way ordinary syringes are prepared with only minimal instructions. It has the ability to keep a free hand behind the bayonet before, during and after injection. No extra accessories are needed to operate the syringe normally. The needle head assembly has the ability to use a variety of needle sizes in conjunction with the same syringe and to provide continued protection after disposal. The needle head assembly is cost effective.

What I claim is:

1. A needle head assembly for use with an ISO luer lock or luer slip syringe, said needle head assembly having a longitudinal center axis comprising:

a luer needle housing having a plunger end and a needle end and a pair of opposing slots located at the needle end thereof;

a plunger axially movable relative to the upper end of said luer needle housing;

a needle holder assembly in the needle end of said needle housing, said holder assembly including a bridge fixed in the needle end of said needle housing;

said bridge including a needle holder that has portions extending in opposite directions from said bridge;

a diaphragm with a center aperture sleeved over one of said portions of said needle holder which faces the plunger end of said needle housing;

said needle holder having a center passage which permits a needle to be inserted and secured therein at the time of assembly;

said one portion of said needle holder extending towards the plunger end of said needle housing thereby permitting different gauges of needles to be used with only one size of said diaphragm;

an actuator having an annular hub with a hollow sheath at one end and a pair of protruding legs at the other end;

said diaphragm having a hollow cavity located between the outer diameter wall of the diaphragm and the inner wall of the diaphragm for receiving said protruding legs of said actuator; and said actuator being located in the needle end of said needle housing where said legs surround said bridge and needle holder and with outer portions of said legs extending through the opposing slots provided in said luer needle housing.

2. The needle head assembly of claim 1, wherein said luer needle housing is in the form of a cylindrical tubular body having an outer walled surface, with the plunger end of said body protruding outwardly from the longitudinal center axis and providing a single ISO luer thread which is of the same configuration as the thread utilized on preexisting luer needle cups.

3. The needle head assembly of claim 2, wherein said one single thread permits the luer needle housing to be attached to the barrel of a luer lock syringe by means of a clockwise twist thereby providing a tight seal between a ISO luer syringe barrel and said luer needle housing.

4. The needle head assembly of claim 1, wherein said actuator legs have a first set of locking protrusions which prevents said actuator sheath from activating prematurely and also prevents said actuator sheath from ingress movement thereby maintaining a covered needle.

5. The needle head assembly of claim 1, wherein said actuator legs have a second set of locking protrusions which lock said actuator legs, hub and sheath in a covered position after an injection has been performed.

6. The needle head assembly of claim 1, wherein a set of protrusions are located in the upper end of said actuator legs, said protrusions facing outwardly from the longitudinal center axis of the assembly.

7. The needle head assembly of claim 6, wherein each protrusion of said last mentioned set of protrusions is tapered on the top edge to permit entrance of said legs into the cavity of said diaphragm.

8. The needle head assembly of claim 7, wherein the bottom edges of said last mentioned set of protrusions are formed at a 90° angle from said legs, said angle permitting said last mentioned actuator legs to lock within the lip on the inside of the outer wall of said diaphragm when said diaphragm and said legs are pushed together thus permitting the actuator and diaphragm to act and move together as a unit.

9. The needle head assembly of claim 1, wherein said plunger has four walls, each wall facing 90° from one another, said walls creating a pedestal for the needle plunger's top and bottom, and a cap provided on the top of the pedestal of said plunger for the purpose of placing downward pressure on the plunger by means of a syringe plunger and piston of the safety syringe to which the needle head assembly is connected via the luer lock.

10. The needle head assembly of claim 9, wherein said cap is formed into a point in order to grip or puncture the soft rubber piston of the plunger of the syringe to which the needle head assembly is attached in order to ensure a straight alignment when contact between the two parts is made and downward pressure is applied to the plunger of the needle head assembly.

11. The needle head assembly of claim 9, wherein the bottom of said pedestal walls of the needle plunger are provided with feet-like extensions for the purpose of seating itself into an upper channel provided in said diaphragm.

12. The needle head assembly of claim 11, wherein said feet-like extensions are beveled or angled thereby permitting easy entrance of said extensions into the diaphragm's upper channel.

13. The needle head assembly of claim 12, wherein said feet-like extensions, once seated into said diaphragm's channel, permit fluid to pass through the diaphragm's center aperture and in between each of said four walls of said needle plunger to minimize the loss of flow into the needle cavity.

14. The needle head assembly of claim 13, wherein said feet-like extensions provided on said plunger act as a base and locking system for said diaphragm whereby said plunger and diaphragm move together as one mechanism when pressure is applied to said plunger.

15. The needle head assembly of claim 1, wherein the activation of the plunger and piston of the syringe to which the needle head assembly is attached makes contact with said plunger of the needle head assembly thereby activating said actuator sheath over the needle by means of downward pressure.

16. The needle head assembly of claim 1, wherein said luer needle housing on opposite sides thereof is provided with finger and thumb rests whereby once the user's finger and thumb are in place on said rests, the user can physically apply downward pressure to the actuator sheath and thereby cover said needle.

17. The needle head assembly of claim 1, wherein the outer wall of said luer needle housing located near the needle end thereof is provided with a small ridge that runs the entire circumference of said housing; and a needle cover cap is provided with a corresponding ridge on the inner surface thereof that runs its entire circumference, said needle cover ridge and said luer needle housing ridge creating a semi-locking barrier.

18. The needle head assembly of claim 17, wherein said needle cover may be removed from said luer needle housing by exerting a light pull thereon so as to override said barrier and with said cover cap removed to expose the sharp needle for delivering an injection.

19. The needle head assembly of claim 18, wherein said needle cover has longitudinal ridges located around the uppermost outer circumference thereof, said longitudinal ridges being provided for the purpose of preventing said needle head assembly from rolling when placed on a flat surface.

20. The needle head assembly of claim 17, wherein the length of said needle, which is premounted in said luer needle housing during assembly, determines the length of said needle cover cap, said cover cap being provided with its own top cap to prevent contamination when used in a field operation.

21. The needle head assembly of claim 9, wherein the bottom of said pedestal walls of the needle plunger is provided with a base of circular configuration, said base having therein a plurality of legs which are spaced apart and separated by slots, said legs having bottom surfaces which seat themselves against the upper surface of said diaphragm when the plunger is depressed.

22. The needle head assembly of claim 21, wherein the bottom surfaces of said legs and the upper surface of said diaphragm are conical surfaces for the purpose of seating themselves together.

23. The needle head assembly of claim 22, wherein said legs, once seated, onto said diaphragm permit fluid to pass through the diaphragm's center aperture and in between each of said four walls of said needle plunger to minimize the loss of flow into the needle cavity.

24. The needle head assembly of claim 23, wherein said legs on the circular base of said plunger form a locking system for said diaphragm whereby said plunger and diaphragm move together as one mechanism when pressure is applied to said plunger.

25. The needle head assembly of claim 1, wherein said luer needle housing is in the form of a cylindrical tubular body having an outer walled surface, with the plunger end of said body protruding outwardly from the longitudinal center axis and providing a plurality of ISO luer threads which are of the same configuration as the threads utilized on preexisting luer needle cups.

26. The needle head assembly of claim 25, wherein said threads permit the luer needle housing to be attached to the barrel of a luer lock syringe by means of a clockwise twist thereby providing a tight seal between a ISO luer syringe barrel and said luer needle housing.

27. The needle head assembly of claim 1, wherein said luer needle housing includes an upper cylindrical housing part and a lower cylindrical housing part which is received in said upper housing part, said upper housing part having said plunger end protruding outwardly from the longitudinal center axis, said upper housing part having an ISO luer thread or threads of the same configuration as the thread or threads utilized on preexisting luer needle cups.

28. The needle head assembly of claim 27, wherein said plunger has four walls, each wall facing 90° from one another, said walls creating a pedestal for the needle plunger's top and bottom, and a cap provided on the top of the pedestal of said plunger for the purpose of placing downward pressure on the plunger by means of a syringe plunger and piston of the safety syringe to which the needle head assembly is connected via the luer lock.

29. The needle head assembly of claim 28, wherein the bottom of said pedestal walls of the needle plunger is provided with a base of circular configuration, said base having therein a plurality of legs which are spaced apart and separated by slots, said legs having bottom surfaces which seat themselves against the upper surface of said diaphragm when the plunger is depressed.

30. The needle head assembly of claim 29, wherein the bottom surfaces of said legs and the upper surface of said diaphragm are conical surfaces for the purpose of seating themselves together.

31. The needle head assembly of claim 30, wherein said legs, once seated, onto said diaphragm permit fluid to pass through the diaphragm's center aperture and in between each of said four walls of said needle plunger to minimize the loss of flow into the needle cavity.

32. The needle head assembly of claim 31, wherein said legs on the circular base of said plunger form a locking system for said diaphragm whereby said plunger and diaphragm move together as one mechanism when pressure is applied to said plunger.

33. The combination of a safety syringe and needle head assembly for administering an injection into tissue, said safety syringe comprising;

a barrel having a plunger and piston movable therein;

said barrel having at the lower end thereof a centrally located cone surrounded by an annular luer lock cup having a plurality of threads;

said needle head assembly having a longitudinal center axis comprising:

a luer needle housing having an outer walled surface, plunger end, a needle end, a pair of opposing slots located in said outer walled surface at the needle end of the luer needle housing;

a plunger axially moveable relative to the upper end of said luer needle housing and extending through said cone into the interior of said barrel when said safety syringe is inactivated;

a needle holder assembly in the needle end of said luer needle housing, said needle holder assembly including a bridge fixed in the needle end of said luer needle housing;

said bridge including a needle holder that has portions extending in opposite directions from said bridge;

a diaphragm with a center aperture sleeved over one of said portions of said needle holder which faces the plunger end of said luer needle housing;

said needle holder having a center passage which permits a needle to be inserted and secured therein at the time of assembly of said needle head assembly;

said one portion of said needle holder extending towards the plunger end of said needle housing thereby permitting different gauges of needles to be used with only one size of said diaphragm;

an actuator having an annular hub with a hollow sheath at one end and a pair of protruding legs at the other end;

said diaphragm having a hollow cavity located between the outer diameter wall of the diaphragm and the inner wall of the diaphragm for receiving said protruding legs of said actuator;

said actuator being located in the needle end of said luer needle housing where said legs surround said bridge and needle holder and with outer portions of said legs extending through the opposing slots provided in said luer needle housing; and said plunger and piston of said safety syringe when activated contacting and depressing the plunger of said needle head assembly thereby activating said actuator sheath and needle for administering an injection of fluid into tissue.

34. The combination of a safety syringe and a needle head assembly of claim 33, wherein said luer needle housing is in the form of a cylindrical tubular body having said outer walled surface, with the plunger end of said body protruding outwardly from the longitudinal center axis and providing a single ISO luer thread which is of the same configuration as the threads utilized in said luer lock cup.

35. The combination of a safety syringe and a needle head assembly of claim 34, wherein said one single thread permits said luer needle housing to be attached to the barrel of said safety syringe by means of a clockwise twist thereby providing a tight seal between said barrel and said luer needle housing.

36. The combination of a safety syringe and a needle head assembly of claim 33, wherein said actuator legs have a first set of locking protrusions which prevent said actuator and said sheath from activating prematurely.

37. The combination of a safety syringe and a needle head assembly of claim 33, wherein said actuator legs have a second set of locking protrusions which lock said actuator legs, hub and sheath in a covered position after an injection has been performed.

38. The combination of a safety syringe and a needle head assembly of claim 33, wherein a set of protrusions are located in the upper end of said actuator legs, said protrusions facing outwardly from the longitudinal center axis of the assembly.

39. The combination of a safety syringe and a needle head assembly of claim 38, wherein each protrusion of said last mentioned set of protrusions is tapered on the top edge to permit entrance of said legs into the cavity of said diaphragm.

40. The combination of a safety syringe and a needle head assembly of claim 39, wherein the bottom edges of said last mentioned set of protrusions are formed at a 90° angle from said legs, said angle permitting said last mentioned actuator legs to lock within the lip on the inside of the outer wall of said diaphragm when said diaphragm and said legs are pushed together thus permitting the actuator and diaphragm to act and move together as a unit.

41. The combination of a safety syringe and a needle head assembly of claim 33, wherein said plunger has four walls, each wall facing 90° from one another, said walls creating a pedestal for the needle plunger's top and bottom, and a cap provided on the top of the pedestal of said plunger for the purpose of placing downward pressure on the plunger by means of said plunger and piston of the safety syringe to which the needle head assembly is connected via the luer lock.

42. The combination of a safety syringe and a needle head assembly of claim 41, wherein said cap is formed into a point in order to grip or puncture the soft rubber piston of the plunger of the syringe to which the needle head assembly is attached in order to ensure a straight alignment when contact between the two parts is made and downward pressure is applied by said plunger and piston of the safety syringe to the plunger of the needle head assembly.

43. The combination of a safety syringe and a needle head assembly of claim 41, wherein the bottom of said pedestal walls of the needle plunger are provided with feet-like extensions for the purpose of seating itself into an upper channel provided in said diaphragm.

44. The combination of a safety syringe and a needle head assembly of claim 43, wherein said feet-like extensions are beveled or angled thereby permitting easy entrance of said extensions into the diaphragm's upper channel.

45. The combination of a safety syringe and a needle head assembly of claim 44, wherein said feet-like extensions, once seated, into said diaphragm's channel permit fluid to pass through the diaphragm's center aperture and in between each of said four walls of said needle plunger to minimize the loss of flow into the needle cavity.

46. The combination of a safety syringe and a needle head assembly of claim 45, wherein said feet-like extensions provided on said plunger act as a base and locking system for said diaphragm whereby said plunger and diaphragm move together as one mechanism when pressure is applied to said plunger by the plunger and piston of the safety syringe.

47. The combination of a safety syringe and a needle head assembly of claim 45, wherein the activation of the plunger and piston of the safety syringe makes contact with and depresses the plunger of the needle head assembly thereby activating said actuator sheath over the needle.

48. The combination of a safety syringe and a needle head assembly of claim 33, wherein said luer needle housing on opposite sides thereof are provided with finger and thumb rests whereby once the user's finger and thumb are in place on said rests, the user can physically apply downward pressure to the actuator sheath and thereby cover the needle.

49. The combination of a safety syringe and a needle head assembly of claim 33, wherein the outer wall of said luer needle housing located near the needle end thereof is provided with a small ridge that runs the entire circumference thereof; and a needle cover cap is provided with a corresponding ridge on the inner surface thereof that runs its entire circumference, said needle cover ridge and said luer needle housing ridge creating a semi-locking barrier.

50. The combination of a safety syringe and a needle head assembly of claim 49, wherein said needle cover may be removed from said luer needle housing by exerting a light pull thereon so as to override said barrier and with said cover cap removed to expose the sharp needle for delivering an injection.

51. The combination of a safety syringe and a needle head assembly of claim 50, wherein said needle cover has longitudinal ridges located around the uppermost outer circumference thereof, said longitudinal ridges being provided for the purpose of preventing the syringe and needle head assembly from rolling when placed on a flat surface.

52. The combination of a safety syringe and a needle head assembly of claim 49, wherein the length of said needle, which is premounted in said luer needle housing during assembly, determines the length of said needle cover cap, said cover cap being provided with its own top cap to prevent contamination when used in a field operation.

* * * * *